US007267646B2

(12) United States Patent
Tucker

(10) Patent No.: US 7,267,646 B2
(45) Date of Patent: Sep. 11, 2007

(54) STIMULATION APPARATUS

(75) Inventor: Martin S. Tucker, Encino, CA (US)

(73) Assignee: Vast Resources, Inc., Chatsworth, CA (US)

(*) Notice: Subject to any disclaimer, the term of this patent is extended or adjusted under 35 U.S.C. 154(b) by 245 days.

(21) Appl. No.: 10/995,830

(22) Filed: Nov. 23, 2004

(65) Prior Publication Data

US 2005/0113636 A1 May 26, 2005

Related U.S. Application Data

(63) Continuation-in-part of application No. 10/688,314, filed on Oct. 17, 2003, now abandoned.

(51) Int. Cl.
*A61F 5/00* (2006.01)

(52) U.S. Cl. ........................................................ 600/38

(58) Field of Classification Search ............ 600/38-41; 128/845

See application file for complete search history.

(56) References Cited

U.S. PATENT DOCUMENTS 2,128,790 A 8/1938 Barbour
4,722,327 A 2/1988 Harvey
4,790,296 A 12/1988 Segal
5,851,175 A 12/1998 Nickell
5,857,960 A 1/1999 Boutos
6,142,929 A 11/2000 Padgett
6,179,795 B1 1/2001 Garza

*Primary Examiner*—John P. Lacyk
(74) *Attorney, Agent, or Firm*—SoCal IP Law Group LLP; Michael D. Harris

(57) ABSTRACT

The stimulation device of the present invention has a reciprocating projecting member that projects out of a slot through the housing. A motor in the housing drives a linkage which converts the motor's rotation into reciprocation. The linkage reciprocates the projecting member. The housing is relatively large and mounts on a horizontal surface. Its weight maintains it in one place during use. The motor and linkage can pivot within the housing to allow the reciprocating member to pivot from a vertical or near vertical orientation to a horizontal or near horizontal orientation. The slot through which the projecting member extends is long enough to permit the projecting member to move between its positions. Therefore, the user can position the projecting member in a position and orientation to contact or enter the user's particular body part.

22 Claims, 6 Drawing Sheets

STIMULATION APPARATUS

RELATED APPLICATIONS

This application is a continuation-in-part of application Ser. No. 10/688,314, filed Oct. 17, 2003 now abandoned.

BACKGROUND OF THE INVENTION

1. Field of the Invention

The present invention is in the field of apparatuses for stimulating humans, primarily sexually stimulating them.

2. General Background and State of the Art

Sexual devices can fall into many different categories, depending on the criteria for the categories. For example, some sexual devices are mere novelties with little practical use. They may be given as joking gifts. A second category includes relatively simple devices used to enhance or change the sexual experience. They may be used by persons seeking to stimulate themselves without another person, or they may be used with another person. They have gained popularity as concerns for sexually transmitted diseases (especially HIV) have increased. Others without sexual partners use then as a substitute for the partner. Many of these devices are battery operated and vibrate. Most of these replicate a human penis or vagina. Contact with the device as it vibrates stimulates the user. The user or his or her partner generates any movement of the device during use.

A third category includes more complex or stand-alone devices that can move relative to the user and vibrate simultaneously. Because they tend to be larger and heavier than battery operated device, the user does not have to hold them. Therefore, the devices have the advantage of freeing the user's arms and hands.

INVENTION SUMMARY

The stimulation device of the present invention has a housing that rests on a usually horizontal surface such as the floor, table or bed. A motor mounts in the housing. As the motor rotates, it drives a linkage that reciprocates a projecting member. The projecting member extends through a slot in the housing. A frame in the housing that mounts the motor allows the reciprocating member to pivot from a vertical or near vertical orientation to a horizontal or near horizontal orientation. The slot through which the projecting member extends is long enough to permit the projecting member to move between its positions. Therefore, one can position the projecting member in a position and orientation to contact or enter the user's particular body part.

The stimulation device of the present invention may accommodate different shaped projecting members for use on different body parts.

Insofar as the stimulation device of the present invention runs on electricity, some of the electricity can power auxiliary devices, especially sexual stimulators such as vibrators. Thus, the present invention may include electrical connections for such other devices. If the principal stimulation device of the present invention runs on home AC current, the device would have a transformer to step down the voltage to the auxiliary devices' voltage. At that low voltage, the connection between the auxiliary device and the main stimulation device can be a small jack, and the power chord between the two devices can be thin-gauge.

BRIEF DESCRIPTION OF THE DRAWINGS

In FIG. 2, the projecting member is vertical, and it is near horizontal in FIG. 3.

DETAILED DESCRIPTION OF THE PREFERRED EMBODIMENTS

Figure 2:
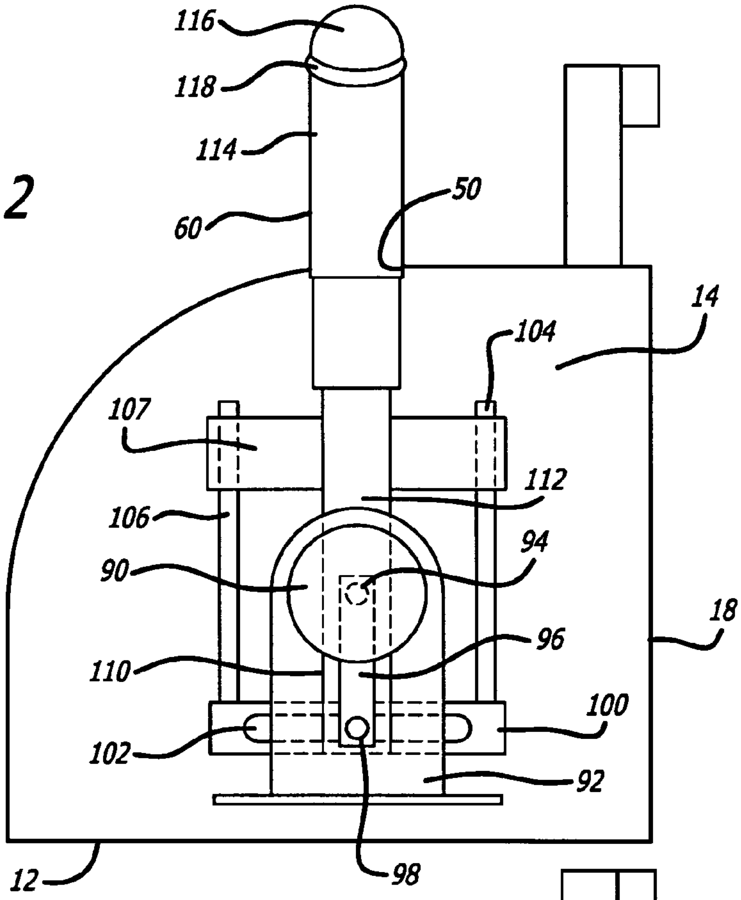
FIGS. 2 and 3 are side views, partially cut away, of an exemplary embodiment of the present invention.
Figure 3:
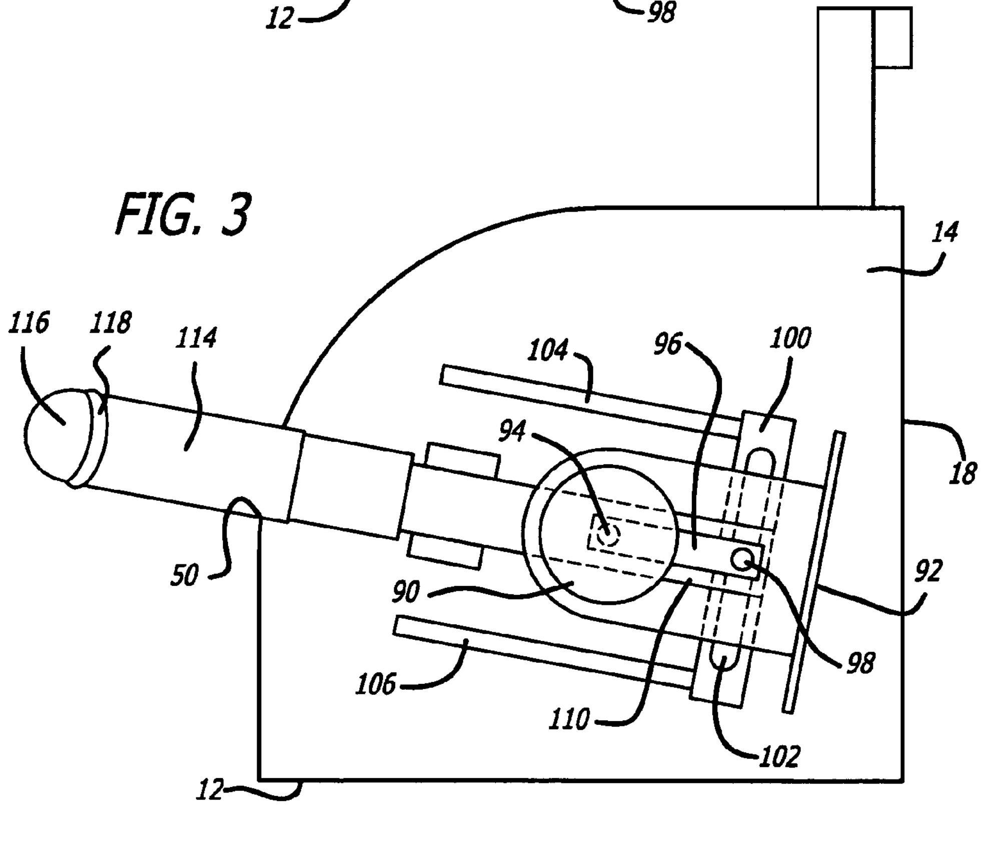

The first exemplary embodiment of the stimulation device of the present invention comprises a housing 10. The housing sits on base 12 (FIGS. 2 and 3). Though the base may have short legs, rubberized pads or some other means for securing the housing to the surface on which it sits such as the floor, a table, a bed or a chair, the drawing show none. The base is square or rectangular in the exemplary embodiment, but other shapes are possible.

Sidewalls 14 and 16 (wall 16 is visible only in FIG. 4) and back wall 18 extend upward from base 12. A curved front/top wall 20 extends from the top of back wall 18 to the front of base 12 between sidewalls 14 and 16. Thus, base 12, sidewalls 14 and 16, back wall 18 and front/top wall 20 form enclosed housing 10. The exemplary embodiment of FIG. 1 also shows an optional flange 22 extending outward from sidewall 14. Another flange would extend from sidewall 16. These flanges add width and stability to the device.

The walls that form the housing may be metal, plastic or some other material. Material and fabrication costs, durability, weight and aesthetics are the main factors affecting the choice of materials.

Figure 1:
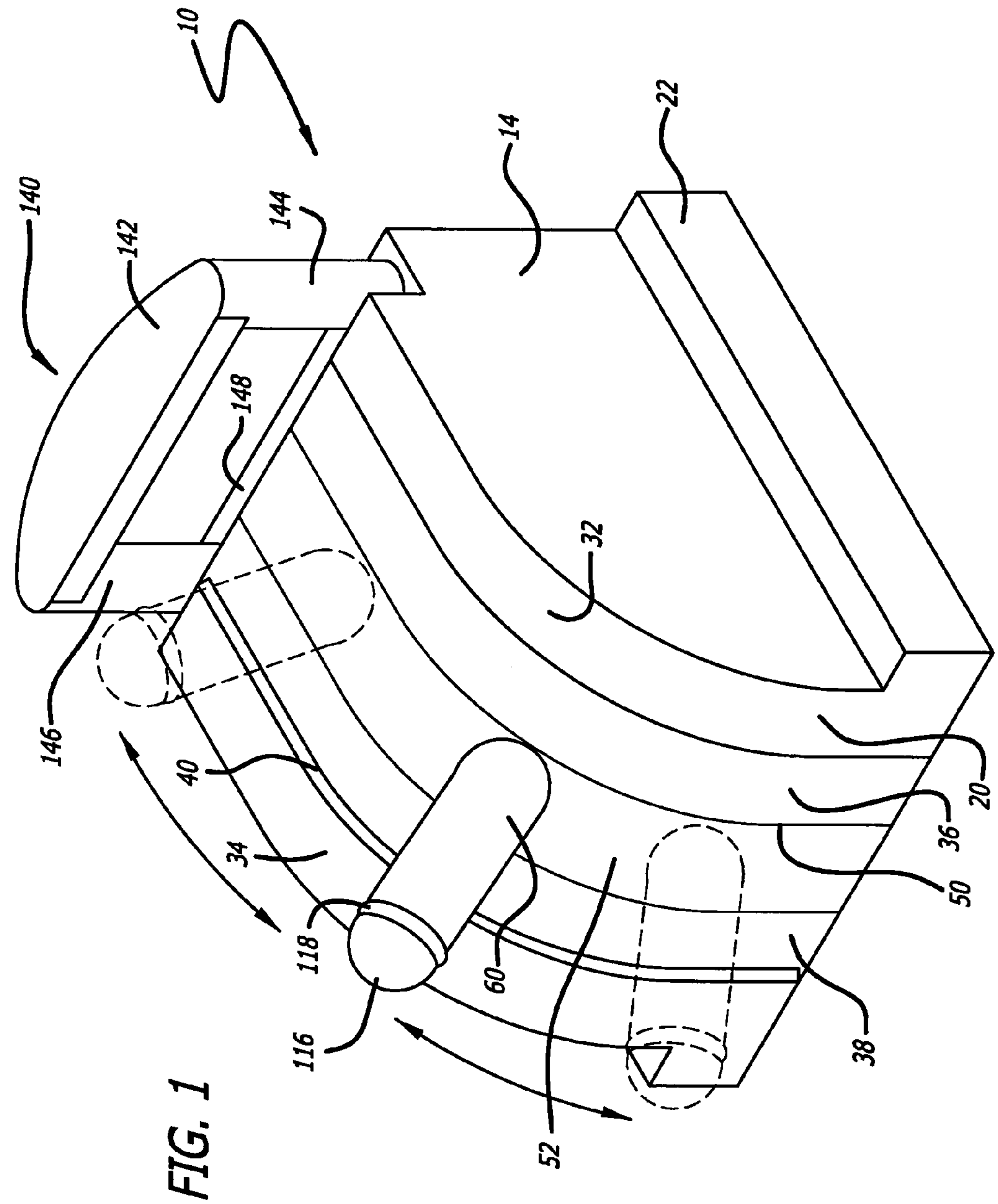
FIG. 1 is a perspective view of an exemplary embodiment of the present invention.

The curved front/top wall 20, which curves from front to back, may be flat from side to side. In the exemplary embodiment, the front/top wall is stepped. That is, outer strips 32 and 34 are raised above inner strips 36 and 38. FIG. 1 shows edge 40 between strips 34 and 38. The pattern could be reversed with the inner strips higher than the outer strips. The strips have constant widths in the exemplary embodiment, but they could taper or be curved.

Figure 4:
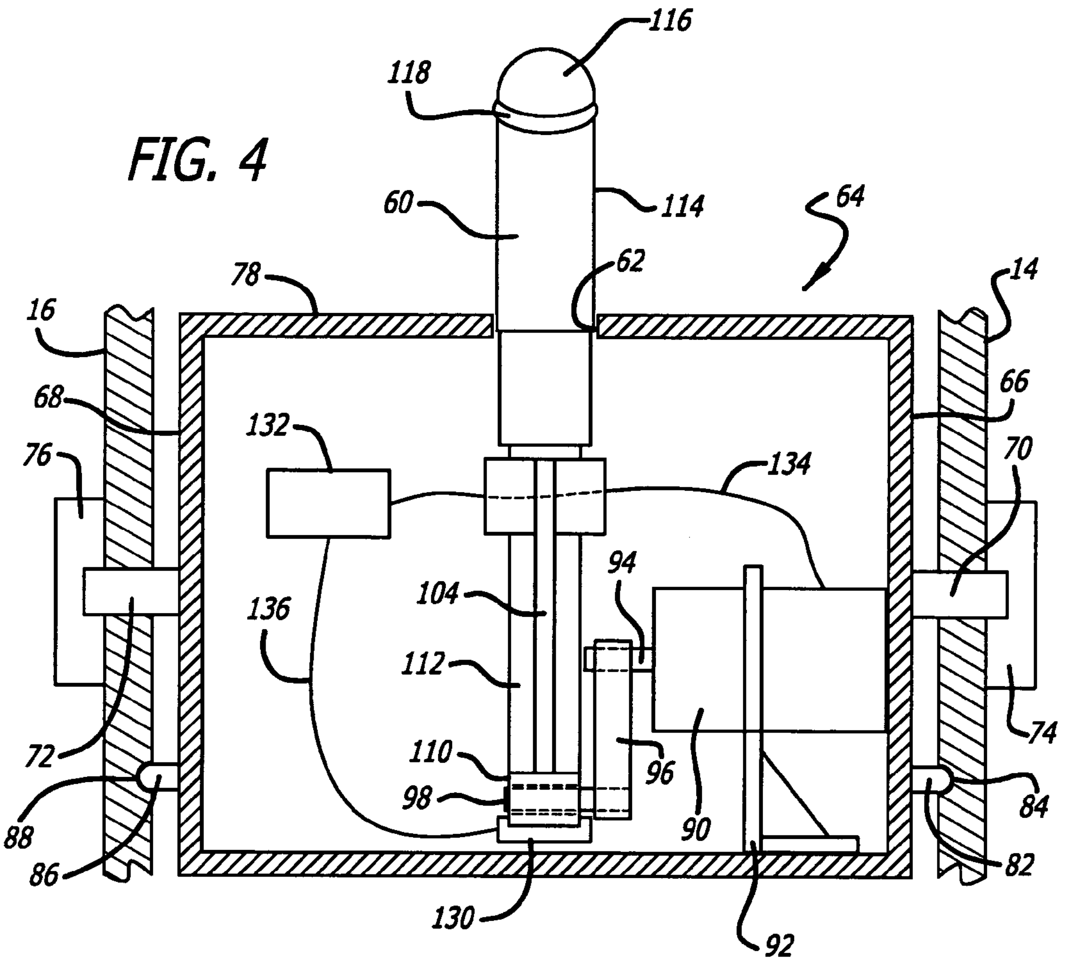
FIG. 4 is a cross-sectional view showing the internal parts of an exemplary embodiment of the present invention.

The inside edges of strips 36 and 38 are spaced apart and form a groove 50 (FIGS. 1 and 4). Projecting member 60 projects out of the groove from inside housing 10. Flexible material 52 may cover the groove to block a user from sticking a finger or hand into the housing. The projecting member pivots from one end of the groove to the other as explained below. The material may move with the projecting member. If so, the material should be long enough that part of it always covers the groove. Flexible materials and construction similar to a roll-top desk could be used. Alternatively, the material may be resilient and stationary with a center groove. As the projecting member reciprocates and moves along groove 50, it pushes the flexible material apart sufficiently to permit the projecting member to move.

Projecting member 60 reciprocates. In the exemplary embodiment, an electric motor 90 mounts on a bracket 92 inside frame 64 (FIG. 4). The motor preferably has a gearbox attached to its output to decrease the rotational velocity of output shaft 94. Many different motors and gear combinations can be used for the proper speed and power. The frame may be metal, plastic or any other suitable material. It can form an enclosure for motor 90 and the parts that the motor operates, or the frame can comprise sufficient braces for required support of the parts.

Two shafts 70 and 72 (FIG. 4) are fixed to sidewalls 66 and 68 of frame 64 and shafts extend through sidewalls 14 and 16 of housing 10 in the exemplary embodiment. Top wall 78 closes the top of the frame. The top wall has an opening 62 through which projecting member 60 extends. The top wall may be omitted, or it may be a brace to hold the frame together. The top wall also could be curved. Accordingly, depending on the size and shape of the top wall, it may replace any flexible material 52 that blocks access to the inside of the housing or the frame.

Optional handles 74 and 76 (FIG. 4) attach to outer ends of shafts 70 and 72. Rotating those handles pivots frame 64 about the axis of the shafts. Thus, the frame and parts attached to the frame pivot with respect to housing 10. The pivoting changes the orientation of projecting member 60. The axes of shaft 70 and 72 could align with the axis of motor shaft 94. With that design, pivoting frame 64 about its axis (through shafts 70 and 72) only rotates the motor. The motor would not move horizontally or vertically. If the curvature of the front/top wall 20 is circular, then the projecting member maintains the same projection out of slot 50 irrespective of its orientation. Avoiding small changes in the nominal distance that projecting member extends out of its slot may not be important, however. If so, the axis of motor shaft 94 could be spaced from the axes of shafts 70 and 72 as FIG. 4 shows. In addition, the curved surface of front/top wall 20 may not be circular, which would change how far the projecting member extends from its slot at different orientations.

Each sidewalls 66 and 68 of the frame 64 may have an optional detent 82 or 86 that biases outward (FIG. 4). The detents engage depressions or holes 84 and 88 in housing sidewalls 14 and 16. The arrangement holds the frame's position relative to the housing, which maintains the orientation of projecting member 60. Other means are available to secure the frame's position. For example, handles 74 and 76 could be treaded to shafts 70 and 72 such that rotating the handles could cause them to frictionally engage the housing's sidewalls 14 and 16. Tightening the handles could also cause the sidewalls of the frame to be pulled toward the housing sidewalls such that washers (not shown) on shaft 70 and 72 would clamp against each other to limit rotation of the frame relative to the housing. Other parts of the frame also could engage other parts of the housing. Moreover, if material 52 in groove 50 (FIG. 1) is resilient and stationary with a center groove, the material's resiliency may be sufficient to hold projecting member 60 to prevent easy movement of the frame relative to the housing.

Figure 10:
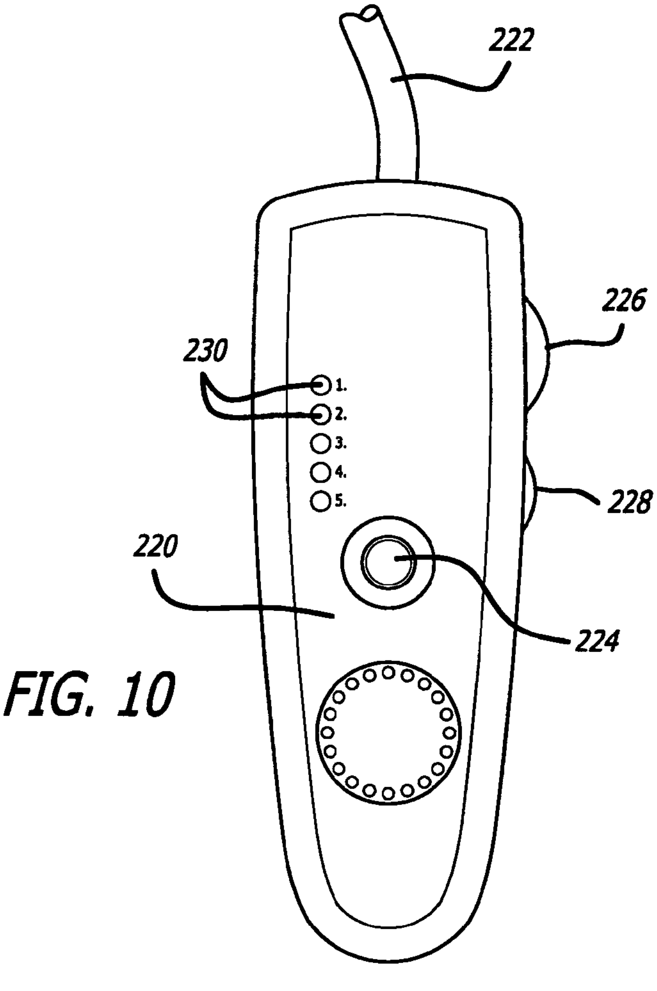
FIG. 10 is plan view of an exemplary remote control device for use with the present invention.

An electric cord (not shown in FIG. 1 but see cord 218 in FIG. 9) extends from outside the housing through one of the housing walls and connects through a fuse to a switch or controller (not shown in FIG. 1 but see the remote controller shown in FIGS. 9 and 10, which is discussed below). The switch or controller electrically connects to the motor and controls whether the motor operates. A controller also may allow adjustments in the motor's speed. As discussed below, the controller also may regulate other available functions for the projecting member.

Crank arm 94 connects to rotating output shaft 92 of motor 90 (FIGS. 2-4). The crank arm is part of a linkage that converts rotation of the motor's output shaft into reciprocation of projecting member 60. Crank arm rotation drives pin 98 at the end of the crank arm. Pin 98 mounts in slot 100 of crosshead assembly 102 (FIGS. 2 and 3). The slot may extend through the crosshead assembly, or the slot may extend into the crosshead assembly deep enough to retain the pin. The crosshead assembly attaches to proximal end 110 of rear portion 112 of projecting member 60. In the exemplary embodiment, the projecting member does not pivot with respect to crosshead assembly 102. Guide rails 104 and 106, which attach to the crosshead assembly, extend through bushings on brace 107. The brace is part of frame 64. The guide rails prevent the crosshead assembly from pivoting. Thus, the guide rails can reciprocate through the bushings. That allows the crosshead assembly to reciprocate. Alternatively, the guide rails could be fixed to the brace and extend through bushings on the crosshead assembly. That arrangement also permits reciprocation of the crosshead assembly.

Therefore, when motor 90 acting through the motor gears rotates motor shaft 94, crank arm 96 revolves with shaft rotation. This movement cause pin 98 to move laterally along the slot 100 of crosshead assembly 102. Because the slot is straight but pin 98 moves circularly, the crosshead assembly reciprocates. Projecting member 60, which attaches to the crosshead assembly also reciprocates relative to slot 50 (FIG. 1).

Projecting member 60 is preferably hollow. Distal portion 114 is smooth, non-corrosive material such as plastic. The surface is cylindrical in the exemplary embodiment, but it may be ribbed or have other shapes. Because the distal portion will contact body parts, it should clean easily. Rear end 112 of the projecting member may be formed integrally with the distal portion, or the two parts may be attached together permanently or by a screw or bayonet fitting. See the discussion about the exemplary embodiments shown in FIGS. 5 and 8*a*, 8*b* and 8*c* for interchangeable distal ends to the projecting member. Allowing the distal portion to separate from the rear portion allows the user to remove the distal portion for cleaning. In addition, the arrangement allows for different distal portions having different sizes and shapes and different functions.

Cap 116 on annular rim 118 (FIG. 4) closes the top of projecting member 60 in the exemplary embodiment. Thus, distal portion 116 of the projecting member resembles a penis. The user inserts the projecting member into a body orifice where it reciprocates. Alternatively, the distal portion could be open at its top so that the hollow inside would receive a body part.

Having projecting member 60 vibrate or perform other functions in addition to the reciprocation may be desirable. Therefore, coupling 130 (FIG. 4) attaches to the proximal end 110 of the projecting member. The coupling can be mounted elsewhere. The coupling can receive various auxiliary apparatuses. For example, an eccentric motor (not shown) can attach to the coupling for vibrating the projecting member. The eccentric motor can be powered by a battery or from house current from the power cord. Though batteries can power the entire apparatus, motor 90 likely will consume too much power for a battery-operated device to run for any substantial length of time.

A heater also may attach to coupling 130 for heating projecting member 60. A pump is another device that can affect the projecting member. A pump could force liquids or air though and out an opening in the top of the projecting member. A pump also could supply suction to the end of the projecting member. Devices cooperating with the projecting member may perform multiple functions simultaneously.

A controller 132 (shown schematically in FIG. 4) electrically connects to the power cord through wires 134 and 136 to motor 90 and the auxiliary device at coupling 130. Switches (not shown in FIG. 1 but see FIGS. 9 and 10), which are accessible to the user, control the controller to control the operation of motor 90 and any auxiliary device. Control for the motor causes it to start or stop and changes the speed of reciprocation of projecting member 60. Similarly, the user can control the auxiliary device by starting the eccentric motor for vibrations or changing the frequency or amplitude of the vibrations.

Handle 140 (FIG. 1) having cross piece 142 mounted on arms 144 and 146 projects out of the top of housing 10. The handle may be fixed, but the arms of the exemplary embodiment can slide into openings in the top wall similar to the way handles of wheeled luggage work. The handle is in its open position in FIG. 1 and allows a user to carry the device easily. So that the handle does not project above the surface of front/top wall 20 when the handle is retracted, that wall has indented ledge 148 that is generally indented enough to receive cross piece 142.

A user carries the entire device to a desired location such as a table, chair, bed or the floor. He or she then positions projecting member 60 to a desired orientation to stimulate a body part. In addition, the housing may have several openings on the rear wall (not shown) that allow a user to attach the device to a hook on a wall or other vertical surface. The user then uses the controller to turn the device on or off and to control reciprocation of the projecting member and any auxiliary device.

Though one might infer from the discussion of the first exemplary embodiment that the device of the present invention is used by one person, couples can use it as an enhancement to other activities.

The housing 210 (FIG. 9) of the second exemplary embodiment of the stimulation device of the present invention is similar to housing 10 of the first exemplary embodiment. A curved front/top wall 212 encloses the top of the housing, and projecting member 214 extends through a slot 216 in the front/top wall. Similar structures described in detail for the first exemplary embodiment pivot and reciprocate the projecting member.

Figure 9:
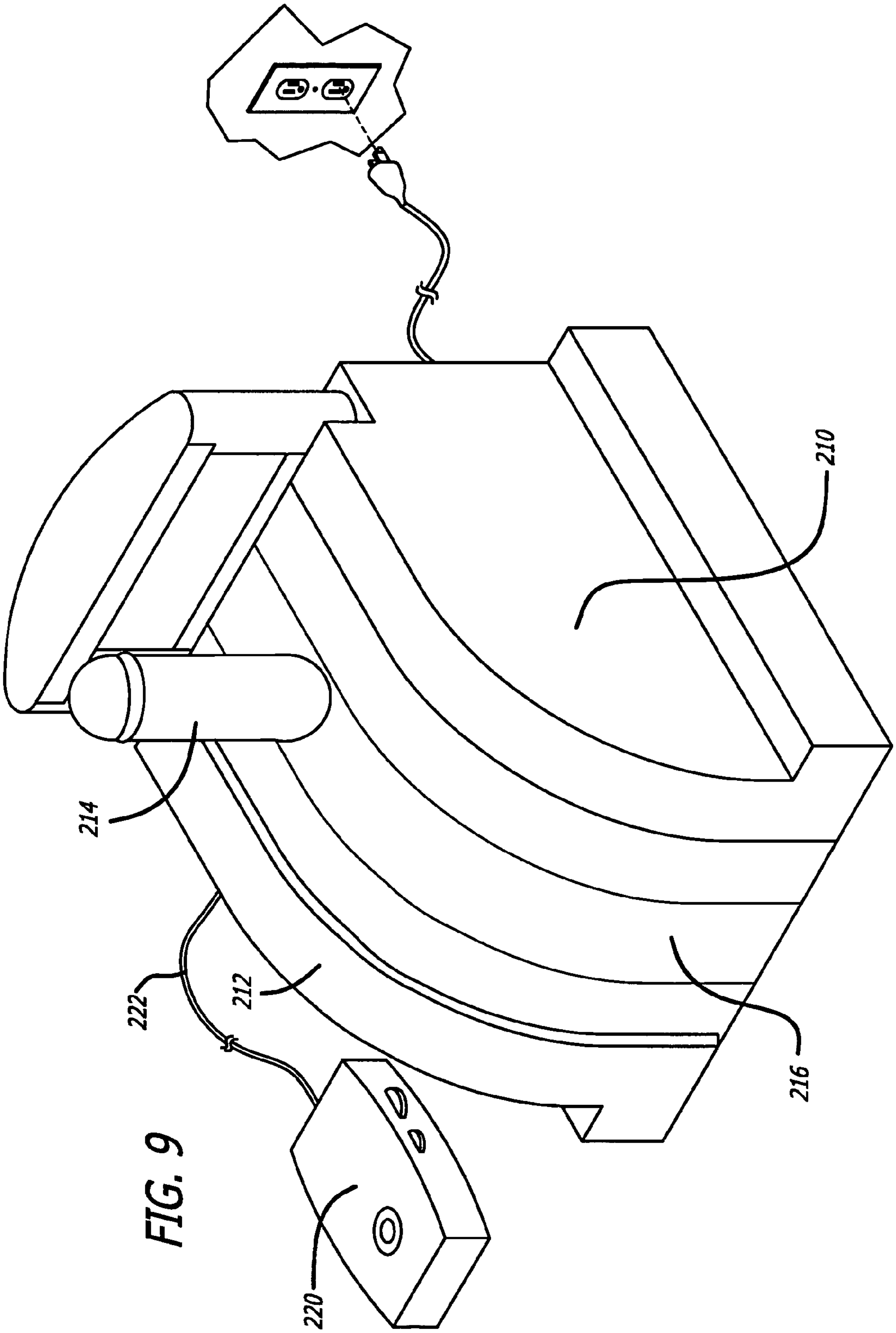
FIG. 9 is a perspective view of a portion of the second exemplary embodiment of the present invention.

In the FIG. 9 embodiment, a remote controller 220 controls the machine of the present invention. In the exemplary embodiment, the controller is hard wired (see cable 222) to the housing. An infrared or radio controlled system could easily replace the hard-wired system. Remote 220 (FIG. 10) has an on/off switch 224 that can turn the entire machine on or off or may just affect the various attachments or vibrations of the projecting member. The outside of the housing 210 (FIG. 9) also could have an on/off switch. In the exemplary embodiment, two dials are provided. One dial 226 adjusts the speed of reciprocation manually, or it may invokes circuitry that changes the reciprocation randomly or by pre-set programs. Repeatedly pressing on/off switch 224 can cause the controller to cycle through different programs. A second dial 228 turns on or off and changes the speed of vibration of the projecting member. The remote has lights such as LEDs 230 to show speed of reciprocation or vibration. Cable 222 should be long enough that the user can use the present invention while holding the remote controller.

Figure 6:
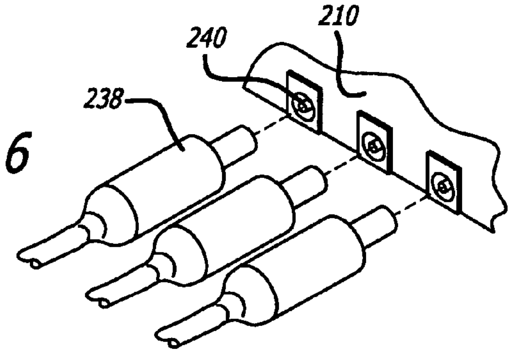
FIG. 6 is a perspective view of a portion of the exemplary housing showing the attachments of auxiliary devices.
Figure 7A:
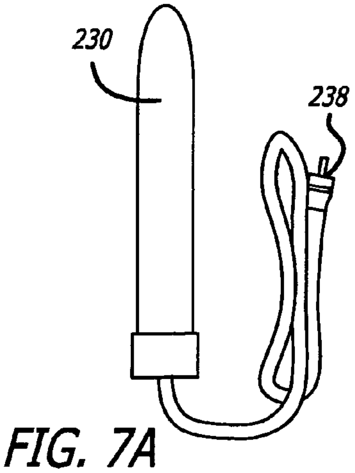
FIGS. 7*a*, 7*b* and 7*c* are side views of exemplary auxiliary stimulators.
Figure 7B:
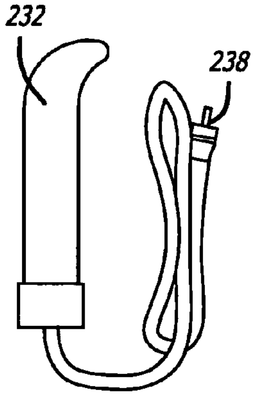
Figure 7C:
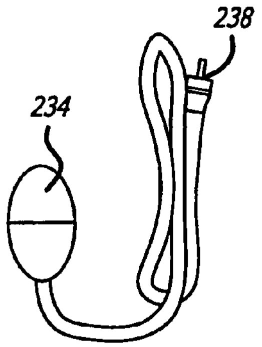

Some users will want stimulation to other body parts during their use of the projecting member for stimulation. Therefore, the present invention can have several vibrators for use with the machine. The exemplary embodiment allows use of up to three vibrators or other accessories. These can be used together or separately. FIGS. 7*a*, 7*b* and 7*c* show possible vibrators 230, 232 and 234. Other shapes are also possible. Each vibrator connects to the housing 210 with a low voltage cable 236. The end of the cable has a plug 238 that plugs into one of the jacks 240 on the housing (FIG. 6). Jacks put out 3V DC power (or another appropriate voltage for the vibrators). A step-down transformer and an AC/DC converter (not shown) convert house power (110V 60 Hz AC for the United States) to 3V DC, the voltage for the exemplary vibrators. Using different voltages for the vibrators or different input voltage or frequencies would require a different transformer.

Vibrator 230 (FIG. 7*a*) is a common shape for sexual vibrators. Vibrator 232 (FIG. 7*b*) is designed to stimulate particular intra-vaginal regions such as the so-called G-spot. Egg-shaped vibrator 234 (FIG. 7*c*) is designed to be held and vibrate within a sexual orifice. The users of the present invention may use one, two or all three vibrators at once. The present invention could supply different exemplary vibrators, and it could have fewer or more than three jacks 240.

Figure 8A:
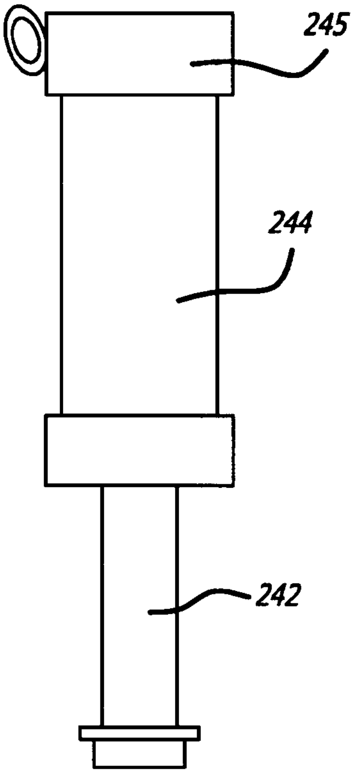
FIGS. 8*a*, 8*b* and 8*c* are side views of exemplary projecting members.
Figure 8B:
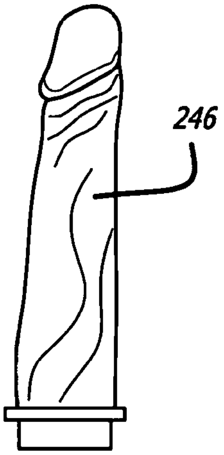
Figure 8C:
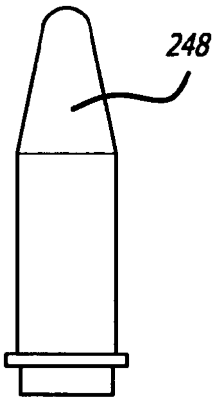

The projecting member may have different shapes as well, and three are shown in FIGS. 8*a*, 8*b* and 8*c*. The projecting member in these embodiments divide into a distal portion and a proximal portion. In FIG. 8*a*, distal portion 240 is an artificial vagina, which comprises a supporting shaft 242 and a receptacle 244. A rim may hold flexible material such as CYBERSKIN®, a product of Topco Sales of Chatsworth, Calif. Portion 246, FIG. 8*b*, is shaped like a penis, and portion 248, FIG. 8*c*, can project into various orifices.

Figure 5:
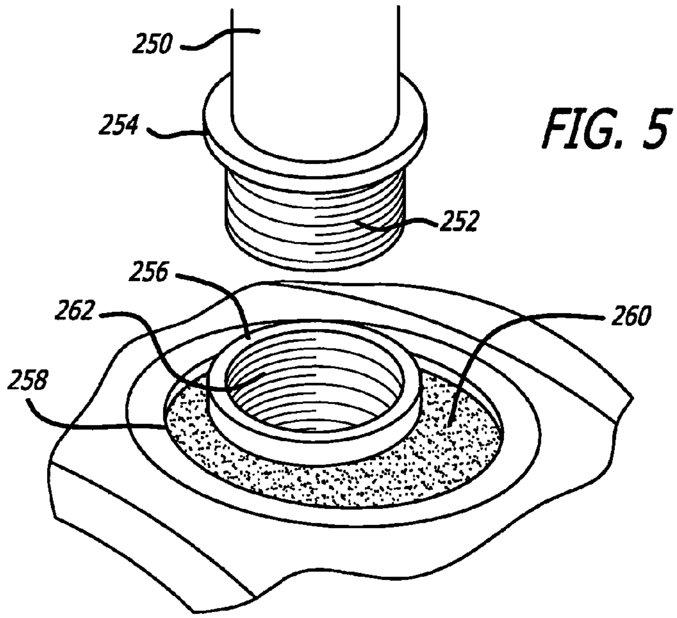
FIG. 5 is a perspective view of a portion of the second exemplary embodiment of the present invention showing the attachment of projecting members to the device.

The inside end 250 of each distal portion 240, 246 and 248 has an external thread 252 below a rim 254 (FIG. 5). Threads 252 on the projecting member thread into internal threads 262 on the proximal portion 256 of that part of the projecting member that is primarily within the housing 210. A flexible splash guard 260 extends from across opening 258 to surround the proximal portion 256 to prevent liquid from going inside the housing.

In lieu of the threaded fitting, a bayonet fitting, a press fit or other connections could attach the proximal and distal portions of the projecting members together. In addition, various other projecting devices can replace or add to the projecting members shown in FIGS. 8*a*, 8*b* and 8*c*. Topco Sales' Web site, http://www.topco-sales.com, has an on-line catalog that shows many feasible projecting members (and vibrators) that could be modified to work with the present invention.

The specification describes particular embodiments of the present invention. Those of ordinary skill can devise variations of the present invention without departing from the inventive concept.

I claim:

1. A stimulation device comprising:

a) a housing, the housing having at least one outside wall and an opening slot through the outside wall;

b) a motor in the housing;

c) a linkage connected to the motor and reciprocating in response to rotation of the motor, d) a projecting member connected to the linkage, the projecting member extending at least partially through the opening slot; the projecting member reciprocating through the slot;

e) the motor and the linkage being pivotable in the housing to change the orientation of the projecting member within the opening slot; and f) a frame in the housing, the frame having a mount for the motor and a mount for the linkage, the frame being mounted for pivoting within the housing whereby the motor and linkage pivot with respect to the housing.

2. The stimulation device of claim 1 further comprising at least one shaft extending between the frame and the housing, the frame pivoting on the at least one shaft relative to the housing.

3. The stimulation device of claim 2 further comprising locking means for locking the frame to the housing in one of a plurality of orientations.

4. The stimulation device of claim 2 wherein the housing has two opposed sidewalls, the device further comprising two coaxial shafts extending between the frame and the two side walls, the frame pivoting about the axis of the shafts.

5. The stimulation device of claim 4 further comprising a handle on at least one of the coaxial shafts on the outside of the housing for pivoting the frame with respect to the housing.

6. A stimulation device comprising:

a) a housing, the housing having at least one outside wall and an opening slot through the outside wall;

b) a motor in the housing;

c) a linkage connected to the motor and reciprocating in response to rotation of the motor, d) a projecting member connected to the linkage, the projecting member extending at least partially through the opening slot; the projecting member reciprocating through the slot;

e) the motor and the linkage being pivotable in the housing to change the orientation of the projecting member within the opening slot; and f) wherein the motor has an output shaft and wherein the linkage comprises a crank arm attached to the output shaft, the crank arm having a pin, the linkage further comprising a crosshead having a lateral slot in the crosshead, the crosshead being connected to the projecting member, the pin projecting into the slot on the crosshead, and means connected to the crosshead for preventing the crosshead from pivoting.

7. The stimulation device of claim 6 further comprising a fitting attached to the projecting member for receiving an auxiliary device for affecting the projecting member.

8. The stimulation device of claim 1 further comprising a cover over the opening slot.

9. The stimulation device of claim 1, wherein the projecting member has a proximal portion substantially inside the housing and a distal portion substantially outside the housing, the proximal and distal portions being separatable from each other.

10. The stimulation device of claim 8 further comprising a rim around the projecting member, the rim extending at least partially through the cover and a splash guard extending from the rim to the projecting member.

11. The stimulation device of claim 1 further comprising a splash guard surrounding the projection member.

12. The stimulation device of claim 1 further comprising at least one electrical jack accessible from the outside of the housing for supplying auxiliary power to an accessory device connectable to the jack.

13. The stimulation device of claim 1 further comprising a power line extending from the housing to a source of electric power and operably connected to the motor, a remote controller operably connected to the motor for controlling the operation of the motor.

14. A stimulation device comprising:

a) a housing, the housing having at least one outside wall and an opening slot through the outside wall;

b) a motor in the housing;

c) a projecting member extending at least partially through the opening slot;

d) reciprocating means operably connecting the motor and the projecting member for reciprocating the projecting member reciprocating through the slot;

e) positioning means attached to the reciprocating means for positioning the projecting member relative to the housing; and f) wherein the positioning means comprises a frame and means for mounting the frame for pivoting within the housing.

15. The stimulation device of claim 14 further comprising locking means for locking the positioning means in one of a plurality of orientations.

16. The stimulation device of claim 14 further comprising a fitting attached to the projecting member for receiving an auxiliary device for affecting the projecting member.

17. The stimulation device of claim 14 further comprising a cover over the opening slot.

18. The stimulation device of claim 14 wherein the projecting member has a proximal portion substantially inside the housing and a distal portion substantially outside the housing, the proximal and distal portions being separatable from each other.

19. The stimulation device of claim 17 further comprising a rim around the projecting member, the rim extending at least partially through the cover and a splash guard extending from the rim to the projecting member.

20. The stimulation device of claim 14 further comprising a splash guard surrounding the projection member.

21. The stimulation device of claim 14 further comprising at least one electrical jack accessible from the outside of the housing for supplying auxiliary power to an accessory device connectable to the jack.

22. The stimulation device of claim 14 further comprising a power line extending from the housing to a source of electric power and operably connected to the motor, a remote controller operably connected to the motor for controlling the operation of the motor.

* * * * *